United States Patent [19]

Inoue et al.

[11] Patent Number: 4,624,920

[45] Date of Patent: Nov. 25, 1986

[54] PROCESS FOR THE PREPARATION OF DICARBOXYLIC ACID USING MICROORGANISM

[75] Inventors: Shigeo Inoue; Yoshiharu Kimura, both of Utsunomiya; Shigehito Adachi, Ichikai, all of Japan

[73] Assignee: Chairman of Research Association for Biotechnology, Eiji Suzuki, Tokyo, Japan

[21] Appl. No.: 673,249

[22] Filed: Nov. 20, 1984

[30] Foreign Application Priority Data

Nov. 25, 1983 [JP] Japan .................................. 58-220683

[51] Int. Cl.[4] ............................ C12P 7/44; C12N 1/20
[52] U.S. Cl. ..................................... 435/142; 435/253; 435/863
[58] Field of Search ............... 435/144, 145, 142, 143, 435/253, 863

[56] References Cited

U.S. PATENT DOCUMENTS 3,419,469 12/1968 Humphrey et al. .................. 435/142
3,773,621 11/1973 Dahlstrom et al. .................. 435/142
3,823,070 7/1974 Minato et al. ........................ 435/143

*Primary Examiner*—Alvin E. Tanenholtz
*Attorney, Agent, or Firm*—Flynn, Thiel, Boutell & Tanis

[57] ABSTRACT

A process for the preparation of a dicarboxylic acid using a thermophilic microorganism, and the microorganism used. The process involves cultivating a microorganism belonging to the genus Mycobacterium which produces a dicarboxylic acid at high temperatures in a medium to which a substrate selected from among normal paraffins, fatty acids, and their derivatives, each containing 6 to 22 carbon atoms, has been added, so that a dicarboxylic acid containing 6 to 22 carbon atoms is formed and accumulated in the medium, and collecting the dicarboxylic acid.

7 Claims, No Drawings

PROCESS FOR THE PREPARATION OF DICARBOXYLIC ACID USING MICROORGANISM

BACKGROUND OF THE INVENTION

1. Field of the Invention

The present invention relates to a process for the preparation of a dicarboxylic acid from a fatty acid derivative using a thermophilic microorganism.

2. Description of Prior Art

Dicarboxylic acids are valuable substances as raw material for the production of synthetic resins, high-quality lubricants, plasticizers, or perfumes. However, the number of carbon atoms of the dicarboxylic acids prepared by the chemical synthesis has been limited, that is, it has been difficult to prepare dicarboxylic acids containing 12 or more carbon atoms. Thus a process for the preparation of dicarboxylic acids by fermentation using microorganisms, in place of the chemical synthesis, has been attracting attention recently.

Most of the microorganisms conventionally employed in the preparation of dicarboxylic acids are yeasts such as microorganisms of the genus Candida (see Japanese Patent Publication No. 19630/1975) or the genus Pichia (see Japanese Patent Publication No. 24392/1970). Only a microorganism of the genus Corynebacterium has been found as a bacterium that can produce dicarboxylic acids (see Japanese Patent Publication No. 17075/1981).

Many fatty acid derivatives, which are used as the substrate for the preparation of a dicarboxylic acid, have a melting point of 40° C. or above. Development of microorganisms that can be employed at temperatures of 40° C. or higher is, therefore, of great interest. Cultivation at high temperatures brings about many advantages, for example, reduction of cooling cost, reduced probability of contamination with germs, decrease in the viscosity of the substrate, increase in the efficiency of contact between the substrate and the microorganism, and the like. However, there have been no microorganisms that can be cultivated at temperatures around 45° C.

SUMMARY OF THE INVENTION

Under these circumstances, the inventors have completed the present invention as the result of searching for microorganisms widely from nature that are capable of converting normal paraffin, fatty acids, or their derivatives into corresponding dicarboxylic acids at temperatures around 45° C., based on the finding that some of the microorganisms belonging to the genus Mycobacterium have such an ability.

More particularly, the present invention is related to a process for the preparation of a dicarboxylic acid using a microorganism, which comprises cultivating a microorganism belonging to the genus Mycobacterium which produces a dicarboxylic acid at high temperatures in a medium to which a substrate selected from among normal paraffins, fatty acids, and their derivatives, each containing 6 to 22 carbon atoms, has been added, so that a dicarboxylic acid containing 6 to 22 carbon atoms can be formed and accumulated in said medium, and collecting said dicarboxylic acid.

DETAILED DESCRIPTION OF THE PREFERRED EMBODIMENTS

The microorganisms used in the present invention belong to the genus Mycobacterium and has an ability of forming a dicarboxylic acid by selectively oxidizing an ω-terminal of a normal paraffin, fatty acid, or its derivative. An example of this microorganism is Mycobacterium sp. KSM-B-33. The strain of this microorganism was separated from soil by the present inventors and deposited with the Fermentation Research Institute of the Agency of Industrial Science and Technology as FERM-P7310 on Oct. 19, 1983, transferred to FERM BP-647 on Nov. 5, 1984 according to Budapest Treaty. The bacteriological characteristics of this microorganism are as follows. The results of the comparison of this microorganism with *Mycobacterium phlei* and *Mycobacterium smegmatis* are shown in Table 1.

(a) Morphology

Slightly curved short bacillus, which is neither motile nor spore-forming. Positive by Gram's stain. Acid-proofness, though not so strong, is recognized. No mycelian growth.

(b) Growth in various media (1) Sucrose-nitrate agar medium:
It grows in abundance in this medium to form a light orange projecting colony with dim luster.

(2) Glucose-asparagine agar medium:
It grows in abundance in this medium to form an orange wrinkled colony with no luster.

(3) Glycerol-asparagine agar medium:
It grows moderately in this medium to form a pink projecting colony. The periphery of the colony is not clear.

(4) Starch agar medium:
It grows moderately in this medium to form an orange projecting colony with dim luster.

(5) Tyrosine agar medium:
It grows moderately in this medium to form a light orange colony with no luster. The periphery of the colony is not clear.

(6) Nutrient agar medium:
It grows moderately in this medium to form a light orange projecting colony with dim luster.

(7) Yeast-malt agar medium:
It grows most abundantly in this medium to form a large dark orange projecting colony with luster.

(8) Oatmeal agar medium:
It grows in abundance in this medium to form an orange wrinkled colony with dim luster.

(c) Physiological Properties (1) Limits of viability:
Temperature: 23° to 51° C. (optimum: 35° to 50° C.)
pH: 2.8 to 9.3 (optimum: 5.3 to 8.5)

(2) Liquefaction of gelatin (glucose-peptone gelatin medium): negative (3) Hydrolysis of starch (starch agar medium): negative (4) Coagulation and peptonization of skimmed milk: both negative (5) Formation of melanin-like chromophore: negative (d) Anabolism on carbon sources
L-arabinose: −
D-xylose: −
D-glucose: +
D-fructose: +
sucrose: ±
inositol: −
L-rhamnose: −
raffinose: −
D-mannitol: ±

(e) Formation of acids and gases from saccharides fructose: +(no formation of gases)
sorbitol: +(no formation of gases)
(f) Composition of cell walls
  diaminopimelic acid: meso type
  saccharide: arabinose, galactose
(g) Mycolic acid (TLC analysis): present
(h) Acid-fast: yes
(i) Source: soil

TABLE 1

| Bacteriological properties | Mycobacterium sp. KSM-B-33 | Mycobacterium phlei (IFO 13160) | Mycobacterium smegmatis (IFO 3153) |
|---|---|---|---|
| (a) Morphology | | | |
| Gram's stain | Positive | Same as the left | Same as the left |
| Shape | Bacillus | Same as the left | Same as the left |
| Spore | Nil | Same as the left | Same as the left |
| Motility | Nil | Same as the left | Same as the left |
| (b) Physiological properties | | | |
| Reduction of nitrates | ± | + | + |
| Denitrification | − | − | − |
| MR test | − | − | − |
| VP test | − | − | − |
| Formation of indole | − | − | − |
| Formation of hydrogen sulfate | − | − | − |
| Hydrolysis of starch | − | − | − |
| Utilization of citric acid | | | |
| Koser's medium | − | − | − |
| Christensen's medium | − | − | − |
| Utilization of inorganic nitrogen sources | | | |
| Nitrate | − | − | − |
| Ammonium salt | − | − | − |
| Formation of chromophore | Orange-colored chromophore | Yellow-colored chromophore | − |
| Christensen's medium | + | + | + |
| SSR's medium | + | + | + |
| Oxidase | − | − | − |
| Catalase | + | + | + |
| Limits of viability | 23 to 51° C. (optimum 35 to 50° C.) | | |
| Sensibility to oxygen | Facultative anaerobic | Facultative anaerobic | Facultative anaerobic |
| OF test | Oxidation | Negative | Oxidation |
| pH range of viability | 2.8 to 9.3 (optimum 5.3 to 8.5) | | |
| Acid-fast | + | + | + |
| (c) Anabolism on carbon sources | | | |
| Glucose | + | − | + |
| Mannose | − | − | ± |
| D-Fructose | + | − | + |
| Galactose | − | − | − |
| Lactose | − | − | − |
| Maltose | − | − | − |
| Sucrose | ± | − | − |
| Trehalose | − | − | − |
| Raffinose | − | − | − |
| D-Sorbitol | − | − | ± |
| Inositol | − | − | ± |
| Glycerol | − | − | + |
| D-Arabinose | − | − | − |
| D-Xylose | − | − | + |
| Inulin | − | − | − |
| Soluble starch | − | − | − |
| α-Methyl-D-glucoside | − | − | − |
| (d) Cell wall composition (TLC analysis) | | | |
| Diaminopimelic acid | Meso-type | Meso-type | Meso-type |
| Saccharide | | | |
| Galactose | + | + | + |
| D-Arabinose | + | + | + |
| D-Xylose | − | − | − |
| Mycolic acid | + | + | + |

(Note) ±: weak

As the result of searching the microorganism having the above properties according to Bergey's *Manual of Determinative Bacteriology* (8th edition, 1975), it was found that said strain belongs to the genus Mycobacterium.

The normal paraffins, fatty acids, or their derivatives used as raw materials in the present invention are those containing 6 to 22, preferably 12 to 18 carbon atoms. The normal paraffin may be a single normal paraffin containing a certain number of carbon atoms or a mixture of two or more normal paraffins containing a different number of carbon atoms. The normal paraffins used in the present invention include, for example, n-hexane, n-heptane, n-nonane, n-decane, n-undecane, n-dodecane, n-tridecane, n-tetradecane, n-hexadecane, n-octadecane, n-nonadecane, n-eicosane, n-heneicosane, and n-docosane. The fatty acids used in the present invention include, for example, caproic, heptanoic, caprylic, nonanoic, decanoic, lauric, myristic, palmitic, stearic, eicosanoic, and docosanoic acids. A lower alkyl ester of a fatty acid is preferred as the fatty acid derivative used in the present invention, which includes, for example, methyl esters, ethyl esters, n- (or iso-)propyl esters, and n- (or sec- or tert-)butyl esters of the above fatty acids.

The composition of the medium used in the present invention comprises an appropriate carbon source, nitrogen source, organic nutrient source, or inorganic salt, in which the strain used can be grown well and successfully produce a dicarboxylic acid from a normal paraffin, fatty acid, or their derivative. Any utilizable carbon sources, including carbohydrates (e.g. glucose, fructose, sucrose, mannitol, etc.), organic acids (e.g. citric acid, succinic acid, fatty acids or the esters thereof), hydrocarbons (e.g. n-dodecane, n-hexadecane, etc.) and the like can be used. As the nitrogen or organic nutrient source, nitrates including sodium nitrate, potassium nitrate, and ammonium nitrates, yeast or meat extract, or peptone can be used. Various phosphates or magnesium sulfate can be used as the inorganic salt. A trace amount of heavy metal salts is further added, but it is not always necessary when the medium contains natural substances. In case a nutrient-requiring mutant is used, a substance which satisfies the requirement must be added to the medium.

The strain is cultivated by sterilizing the medium by heating or other method, inoculating the strain into the medium, and shaking or agitating under aeration the culture for 3 to 5 days at a temperature ranging from 40° to 50° C. Better results are obtained by adjusting the pH value at 6.5 to 8. When a carbon source which is difficultly soluble in water is used, polyoxyethylene sorbitan or other surface active agents may be added.

The obtained culture can be used as an enzyme source as it is, or the bacterium can be separated from the culture liquid by an ordinary method of separating a solid from a solution. The separated vital bacterium and the treatment products thereof (lyophilized bacterium, etc.) can also be used as enzyme source.

A dicarboxylic acid is produced by cultivating the strain of the present microorganism in the manner just described, using a normal paraffin, fatty acid, or its derivative as reaction substrate. A substrate containing 12 to 18 carbon atoms is especially preferable, and a lower alkyl ester of a fatty acid is preferred as the fatty acid derivative.

A dicarboxylic acid, which is the desired substance, can be collected and purified according to an ordinary method of collecting and purifying ordinary organic compounds. For example, a filtrate obtained by removing the culture liquid of the bacterium and the like, or the entire culture liquid is acidified, from which the desired substance is extracted with an organic solvent such as ethyl ether, ethyl acetate, or a chloroform-methanol mixture. The desired dicarboxylic acid can be isolated from the extract by column chromatography, recrystallization, or other methods.

The dicarboxylic acid-producing microorganism used in the present invention was collected as follows:

About 0.5 g of the collected soil sample was suspended in 10 ml of sterilized water. 0.2 ml of the suspension, after it was fully stirred, was inoculated into 10 ml of a liquid medium (I) having the following composition (in a 50 ml test tube) and subjected to shaking for 4 days at 30° C.

| Liquid medium (I)* | Composition |
|---|---|
| n-hexadecane | 100 g |
| $(NH_4)_2SO_4$ | 20 g |
| $KH_2PO_4$ | 2 g |
| yeast extract | 2 g |
| $MgSO_4.7H_2O$ | 500 mg |
| $FeSO_4.7H_2O$ | 10 mg |
| $MnSO_4.4-6H_2O$ | 8 mg |
| ion-exchange water | 1 l |
| pH | 7 |

*I. Shiio and R. Uchio, Agr. Biol. Chem., 35(13), 2033–2042 (1971)

The culture liquid proliferated by the above cultivation was appropriately diluted with sterilized water, implanted to a bouillon agar medium (ordinary agar medium; manufactured by Eiken Kagaku) and cultivated for 2 days at 30° C. The implantation to the bouillon agar medium was repeated until it was recognized by the naked eye and microscopically that the produced colonies were not different from each other.

Ten colonies were selected from the above colonies to be inoculated into slant agar media (II) having the following composition, and cultivated for 3 days at 30° C. It was recognized that ten strains on the slant media were the same when observed by the naked eye and microscopically, as well as that the characteristics and physiological properties of these ten strains on each medium were the same.

| Slant agar medium (II) | Composition |
|---|---|
| n-hexadecane | 20 g |
| $(NH_4)_2SO_4$ | 20 g |
| $KH_2PO_4$ | 2 g |
| yeast extract | 2 g |
| $MgSO_4.7H_2O$ | 500 mg |
| $FeSO_4.7H_2O$ | 10 mg |
| $MnSO_4.4-6H_2O$ | 8 mg |
| polyoxyethylene sorbitan monolaurate (average number of EO's: 20 mol) | 50 mg |
| agar | 20 g |
| ion-exchange water | 1 l |
| pH | 7 |

The characteristics and physiological properties of said strains on the media were as described previously. As the result of the test described above, these ten cultivated bacteria were proved to be a single strain purely separated from nature.

One loop of the purely cultivated strain on the slant medium was suspended in sterilized 10% aqueous glycerol solution (2 ml) in a vial for freeze-storage, and freeze-stored at −80° C. After 3 months' freeze-storage, the suspension was rapidly thawed, and one loop of the thawed suspension was revived on the bouillon agar media. As the result of the examination of the characteristics and physiological properties of the revived strains on each medium, it was found that the strains underwent no changes from the state before the freezing.

The similar examination of the characteristics and physiological properties of the strains on each medium was made after repeating said freezing and thawing five times per month, but no changes were recognized either.

The present invention will be described in more detail by the following examples. However, these examples are not intended to limit the scope of the present invention.

EXAMPLE 1

50 g of methyl palmitate, 10 g of ammonium secondary phosphate, 2 g of potassium primary phosphate, 0.2 g of magnesium sulfate (heptahydrate), 0.02 g of ferrous sulfate (heptahydrate), 0.016 g of zinc sulfate (heptahydrate), 0.016 g of manganese sulfate (tetra- to hexahydrate), and 2 g of yeast extract were dissolved in tap water so that the total amount of the solution was 1 l, and adjusted to pH 7.0. 5 ml of this liquid medium was charged in a 50 ml shaking test tube, sterilized with steam at 120° C. for 15 minutes, inoculated with one loop of Mycobacterium sp. KSM-B-33, and subjected to shaking culture for 120 hours at 45° C.

After the cultivation was completed, 1 ml of 9N sulfuric acid was added to the culture liquid to make the liquid strongly acidic, to which 20 ml of a chloroform-methanol (2:1) mixture was added for extraction. The liquid extract was concentrated under a reduced pressure and methylated with methanol/$BF_3$ catalyst. The obtained product was determined by gas chromatography, the results of which are shown in Table 2.

As the GC-MS data of the product agreed with those of the authentic sample, the product was identified as α,ω-tetradecanedicarboxylic acid.

TABLE 2

| Product/Experiment No. | (1) | (2) |
|---|---|---|
| α, ω-tetradecanedicarboxylic acid | 13 | 9 |

TABLE 2-continued

| Product/Experiment No. | (1) | (2) |
|---|---|---|
| (mg/l culture liquid) | | |

EXAMPLE 2

50 g of methyl palmitate, 10 g of ammonium secondary phosphate, 2 g of potassium primary phosphate, 0.2 g of magnesium sulfate (heptahydrate), 1 g of polypeptone, and 2 g of yeast extract were dissolved in tap water so that the total amount of the solution was 1 l, and adjusted to pH 7.0. 50 ml of this liquid medium was charged in a 500 ml shaking flask, sterilized with steam at 120° C. for 15 minutes, inoculated with one loop of Mycobacterium sp. KSM-B-33, and subjected to shaking culture for 132 hours at 45° C.

After the cultivation was completed, 10 ml of 9N sulfuric acid was added to the culture liquid to make the liquid strongly acidic, to which 100 ml of ethyl ether was added for extraction. The extract was dried over anhydrous sodium sulfate, concentrated under a reduced pressure, and methylated with methanol/BF$_3$ catalyst. The product was determined by gas chromatography. As the result of the determination, it was found that α,ω-tetradecanedicarboxylic acid was obtained in an amount of 13 mg per liter of the culture liquid. As the GC-MS data of the product agreed with those of the authentic sample, the product was identified as α,ω-tetradecanedicarboxylic acid.

EXAMPLE 3

The cultivation was made using Mycobacterium sp. KSM-B-33 as strain, under the same conditions as those in Example 1 except that various carbon sources shown in Table 3 were used as reaction substrate in place of methyl palmitate. The results are shown in Table 3.

TABLE 3

| Carbon source | Product | (mg/l culture liquid) |
|---|---|---|
| n-hexadecane | α, ω-tetradecanedicarboxylic acid | 11 |
| palmitic acid | α, ω-tetradecanedicarboxylic acid | 7 |
| isopropyl palmitate | α, ω-tetradecanedicarboxylic acid | 16 |
| ethyl laurate | α, ω-decanedicarboxylic acid | 5 |
| ethyl oleate | α, ω-hexadecenedicarboxylic acid | 3 |

The embodiments of the invention in which an exclusive property or privilege is claimed are defined as follows:

1. A process for preparing a dicarboxylic acid containing from 6 to 22 carbon atoms, which comprises: culturing the microorganism Mycobacterium sp. KSM-B-33 (FERM BP-647), at a temperature in the range of from 40° to 50° C., under aerobic conditions, in a culture medium containing a nitrogen source and containing, as a carbon source, a substance capable of being transformed to said dicarboxylic acid by the action of said microorganism, said substance containing from 6 to 22 carbon atoms and being selected from the group consisting of normal paraffins, fatty acids and lower alkyl esters of said fatty acids, and recovering said dicarboxylic acid that is formed in the culture medium.

2. The process as set forth in claim 1, wherein said dicarboxylic acid-producing microorganism has the following characteristics:
(a) Morphology
Slightly curved short bacillus, which is neither motile nor spore-forming. Positive by Gram's stain. Acid-proofness, though not so strong, is recognized. No mycelian growth;
(b) Growth in various media
(1) Sucrose-nitrate agar medium: it grows in abundance in this medium to form a light orange projecting colony with dim luster;
(2) Glucose-asparagine agar medium: It grows in abundance in this medium to form an orange wrinkled colony with no luster;
(3) Glycerol-asparagine agar medium: It grows moderately in this medium to form a pink projecting colony. The periphery of the colony is not clear;
(4) Starch agar medium: It grows moderately in this medium to form an orange projecting colony with dim luster;
(5) Tyrosine agar medium: It grows moderately in this medium to form a light orange colony with no luster. The periphery of the colony is not clear;
(6) Nutrient agar medium: It grows moderately in this medium to form a light orange projecting colony with dim luster;
(7) Yeast-malt agar medium: It grows most abundantly in this medium to form a large dark orange projecting colony with luster;
(8) Oatmeal agar medium: It grows in abundance in this medium to form an orange wrinkled colony with dim luster;
(c) Physiological Properties
(1) Limits of viability: Temperature: 23° to 51° C. (optimum: 35° to 50° C.) pH: 2.8 to 9.3 (optimum: 5.3 to 8.5)
(2) Liquefaction of gelatin (glucose-peptone gelatin medium): negative
(3) Hydrolysis of starch (starch agar medium): negative
(4) Coagulation and peptonization of skimmed milk: both negative
(5) Formation of melanin-like chromophore: negative
(d) Anabolism on carbon sources
L-arabinose: —
D-xylose: —
D-glucose: +
D-fructose: +
sucrose: ±
inositol: —
L-rhamnose: —
raffinose: —
D-mannitol: ±
(e) Formation of acids and gases from saccharides
fructose: +(no formation of gases)
sorbitol: +(no formation of gases)
(f) Composition of cell walls
diaminopimelic acid: meso type
saccharide: arabinose, galactose
(g) Mycolic acid (TLC analysis): present
(h) Acid-fast: yes.

3. The microorganism Mycobacterium sp. KSM-B-33 (FERM BP-647) having the following characteristics:
(a) Morphology
Slightly curved short bacillus, which is neither motile nor spore-forming. Positive by Gram's stain. Acid-proofness, though not so strong, is recognized. No mycelian growth;

(b) Growth in various media
  (1) Sucrose-nitrate agar medium: It grows in abundance in this medium to form a light orange projecting colony with dim luster;
  (2) Glucose-asparagine agar medium: It grows in abundance in this medium to form an orange wrinkled colony with no luster;
  (3) Glycerol-asparagine agar medium: It grows moderately in this medium to form a pink projecting colony. The periphery of the colony is not clear.
  (4) Starch agar medium: It grows moderately in this medium to form an orange projecting colony with dim luster;
  (5) Tyrosine agar medium: It grows moderately in this medium to form a light orange colony with no luster. The periphery of the colony is not clear;
  (6) Nutrient agar medium: It grows moderately in this medium to form a light orange projecting colony with dim luster;
  (7) Yeast-malt agar medium: It grows most abundantly in this medium to form a large dark orange projecting colony with luster;
  (8) Oatmeal agar medium: It grows in abundance in this medium to form an orange wrinkled colony with dim luster;

(c) Physiological Properties
  (1) Limits of viability: Temperature: 23° to 51° C. (optimum: 35° to 50° C.) pH: 2.8 to 9.3 (optimum: 5.3 to 8.5)
  (2) Liquefaction of gelatin (glucose-peptone gelatin medium): negative
  (3) Hydrolysis of starch (starch agar medium): negative
  (4) Coagulation and peptonization of skimmed milk: both negative
  (5) Formation of melanin-like chromophore: negative (d) Anabolism on carbon sources
  L-arabinose: —
  D-xylose: —
  D-glucose: +
  D-fructose: +
  sucrose: ±
  inositol: —
  L-rhamnose: —
  raffinose: —
  D-mannitol: ±

(e) Formation of acids and gases from saccharides
  fructose: +(no formation of gases)
  sorbitol: +(no formation of gases)

(f) Composition of cell walls
  diaminopimelic acid: meso type,
  saccharide: arabinose, galactose (g) Mycolic acid (TLC analysis): present (h) Acid-fast: yes.

4. The process as set forth in claim 1, wherein said substance is a member of the group consisting of methyl palmitate, n-hexadecane, palmitic acid, isopropyl palmitate, ethyl laurate and ethyl oleate.

5. The process as set forth in claim 1, wherein said substance contains from 12 to 18 carbon atoms.

6. The process as set forth in claim 1, wherein said normal paraffin is selected from the group consisting of n-hexane, n-heptane, n-nonane, n-decane, n-undecane, n-dodecane, n-tridecane, n-tetradecane, n-hexadecane, n-octadecane, n-nonadecane, n-eicosane, n-heneicosane and n-docosane, said fatty acid is selected from the group consisting of caproic, heptanoic, caprylic, nonanoic, decanoic, lauric, myristic, palmitic, stearic, eicosanoic, and docosanoic acids, and said fatty acid esters are selected from among the group consisting of methyl esters, ethyl esters, n-propyl esters, isopropyl esters, n-butyl esters, sec-butyl esters, and tert-butyl esters of caproic, heptanoic, caprylic, nonanoic, decanoic, lauric, myristic, palmitic, stearic, eicosanoic, and docosanoic acids.

7. The process as set forth in claim 1, wherein the culturing is carried out at a temperature of about 45° C.

* * * * *